United States Patent
Nakabayashi

(10) Patent No.: US 8,204,088 B2
(45) Date of Patent: Jun. 19, 2012

(54) WAVELENGTH TUNABLE LASER AND OPTICAL TOMOGRAPHY SYSTEM USING THE WAVELENGTH TUNABLE LASER

(75) Inventor: Kouki Nakabayashi, Ashigarakami-gun (JP)

(73) Assignees: FUJIFILM Corporation, Tokyo (JP); Fujinon Corporation, Saitama-shi (JP)

( * ) Notice: Subject to any disclaimer, the term of this patent is extended or adjusted under 35 U.S.C. 154(b) by 1480 days.

(21) Appl. No.: 11/723,820

(22) Filed: Mar. 22, 2007

(65) Prior Publication Data

US 2007/0239035 A1    Oct. 11, 2007

(30) Foreign Application Priority Data

Mar. 22, 2006   (JP) ................................ 2006-079370
Mar. 31, 2006   (JP) ................................ 2006-099108

(51) Int. Cl.
    *H01S 3/123* (2006.01)
    *H01S 3/11* (2006.01)
    *H01S 3/08* (2006.01)

(52) U.S. Cl. .............................. 372/15; 372/20; 372/99

(58) Field of Classification Search .................... 372/15, 372/20, 16, 99
See application file for complete search history.

(56) References Cited

U.S. PATENT DOCUMENTS

| | | | |
|---|---|---|---|
| 7,099,358 B1 | 8/2006 | Chong | |
| 2005/0035295 A1* | 2/2005 | Bouma et al. | 250/341.1 |

FOREIGN PATENT DOCUMENTS

JP    2007042971 A    2/2007

OTHER PUBLICATIONS

Japanese Office Action for Application No. 2006-099108, dated Feb. 1, 2011.
Japanese Office Action for Application No. 2006-079370 issued Feb. 22, 2011.
R. Huber, et al., "Amplified, frequency swept lasers for frequency domain reflectometry and OCT imaging: design and scaling principles", Optics Express, 2005, pp. 3513-3528, vol. 13, No. 9, Massachusetts Institute of Technology, Cambridge, MA.
Mitsuo Takeda, "Optical Frequency Scanning Interference Microscopes", Optics Engineering Contact, 2003, pp. 426-432, vol. 41, No. 7.

* cited by examiner

*Primary Examiner* — Armando Rodriguez
(74) *Attorney, Agent, or Firm* — Sughrue Mion, PLLC

(57) ABSTRACT

An external resonator type wavelength tunable laser has a laser medium, a dispersion system which spatially disperses light emitted from the laser medium by wavelength, and a wavelength selecting system having a reflecting surface which selectively reflects a part of the light which is reflected by the reflecting surface as a return light, and the wavelength selecting system is structured so that the inverse of a number of a wavelength of the return light linearly changes with time.

6 Claims, 13 Drawing Sheets

FIG.4

| PARAMETER | | SYMBOL | VALUE | UNIT |
|---|---|---|---|---|
| LIGHT VELOCITY | | c | 3E-11 | mm/sec |
| FREQUENCY OF THE ROTATIONAL BODY | * | ω | 20000 | Hz |
| NUMBER OF THE REFLECTING SURFACE | * | N | 20 | PATTERN |
| SWEEPING PERIOD | | T | 0.0000025 | sec |
| DISK ROTATION ANGULAR VELOCITY | | α | 125663.71 | rad/sec |
| FREQUENCY OF THE RETURN LIGHT UPON INITIATION | * | $v_0$ | 2.61E+14 | 1/sec |
| FREQUENCY OF THE RETURN LIGHT UPON END | * | $v_T$ | 3.16E+14 | 1/sec |
| REFLECTING POSITION X-COORDINATE | * | $x_0$ | -15.0 | mm |
| REFLECTING POSITION Y-COORDINATE UPON INITIATION | * | $y_0$ | 20.0 | mm |
| REFLECTING POSITION Y-COORDINATE UPON END | * | $y_T$ | 12.0 | mm |

| n | t | $v(t)$ | $\lambda(t)$ | REFLECTING POSITION | | REFLECTING SURFACE | | |
|---|---|---|---|---|---|---|---|---|
| | | | | x(t) | y(t) | αt | θ(t) | r(t) |
| 0 | 0.000000000 | 2.61E+14 | 0.00115 | -15.0 | 20.0 | 0.0 | -36.87 | 25.00 |
| 1 | 0.000000013 | 2.64E+14 | 0.00114 | -15.0 | 19.6 | 0.9 | -36.53 | 24.68 |
| 2 | 0.000000025 | 2.66E+14 | 0.00113 | -15.0 | 19.2 | 1.8 | -36.20 | 24.36 |
| 3 | 0.000000038 | 2.69E+14 | 0.00111 | -15.0 | 18.8 | 2.7 | -35.89 | 24.05 |
| 4 | 0.000000050 | 2.72E+14 | 0.00110 | -15.0 | 18.4 | 3.6 | -35.59 | 23.74 |
| 5 | 0.000000063 | 2.75E+14 | 0.00109 | -15.0 | 18.0 | 4.5 | -35.31 | 23.43 |
| 6 | 0.000000075 | 2.77E+14 | 0.00108 | -15.0 | 17.6 | 5.4 | -35.04 | 23.12 |
| 7 | 0.000000088 | 2.80E+14 | 0.00107 | -15.0 | 17.2 | 6.3 | -34.79 | 22.82 |
| 8 | 0.000000100 | 2.83E+14 | 0.00106 | -15.0 | 16.8 | 7.2 | -34.56 | 22.52 |
| 9 | 0.000000113 | 2.86E+14 | 0.00105 | -15.0 | 16.4 | 8.1 | -34.35 | 22.23 |
| 10 | 0.000000125 | 2.88E+14 | 0.00104 | -15.0 | 16.0 | 9.0 | -34.15 | 21.93 |
| 11 | 0.000000138 | 2.91E+14 | 0.00103 | -15.0 | 15.6 | 9.9 | -33.98 | 21.64 |
| 12 | 0.000000150 | 2.94E+14 | 0.00102 | -15.0 | 15.2 | 10.8 | -33.82 | 21.36 |
| 13 | 0.000000163 | 2.97E+14 | 0.00101 | -15.0 | 14.8 | 11.7 | -33.68 | 21.07 |
| 14 | 0.000000175 | 2.99E+14 | 0.00100 | -15.0 | 14.4 | 12.6 | -33.57 | 20.79 |
| 15 | 0.000000188 | 3.02E+14 | 0.00099 | -15.0 | 14.0 | 13.5 | -33.47 | 20.52 |
| 16 | 0.000000200 | 3.05E+14 | 0.00098 | -15.0 | 13.6 | 14.4 | -33.40 | 20.25 |
| 17 | 0.000000213 | 3.08E+14 | 0.00098 | -15.0 | 13.2 | 15.3 | -33.35 | 19.98 |
| 18 | 0.000000225 | 3.10E+14 | 0.00097 | -15.0 | 12.8 | 16.2 | -33.32 | 19.72 |
| 19 | 0.000000238 | 3.13E+14 | 0.00096 | -15.0 | 12.4 | 17.1 | -33.32 | 19.46 |
| 20 | 0.000000250 | 3.16E+14 | 0.00095 | -15.0 | 12.0 | 18.0 | -33.34 | 19.21 |

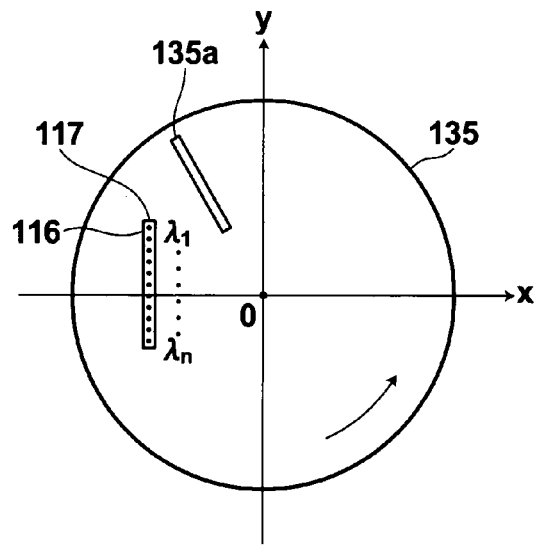
PRIOR ART
FIG.6
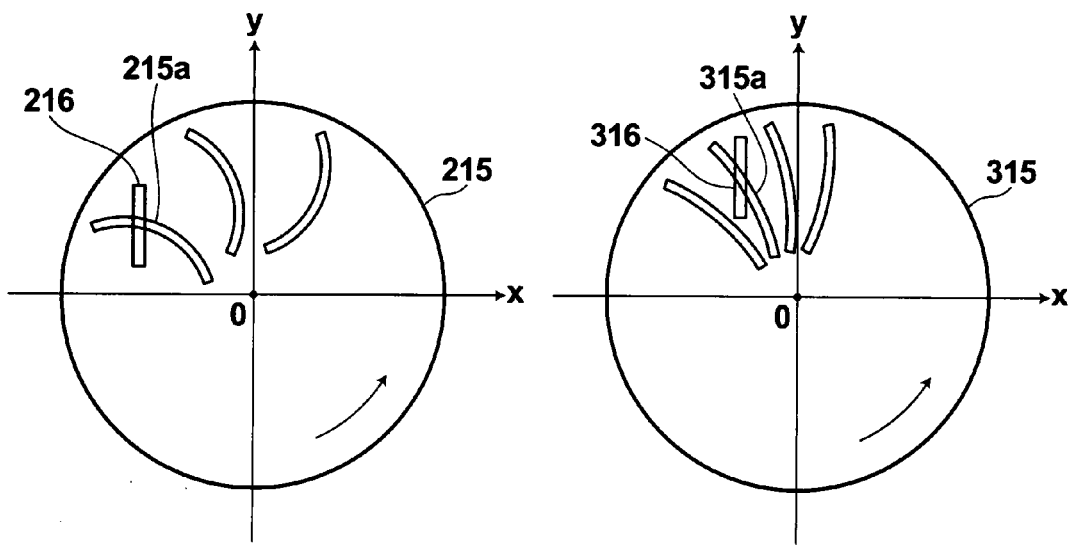
FIG.7A   FIG.7B

FIG.10

| t | ν(t) | λ(t) | θ(t) | θ'(t) | F⁻¹(G(θ')) | DIFFERENCE |
|---|---|---|---|---|---|---|
| 0 | 2.6087E+14 | 0.00115 | 0 | 0 | 0 | 0 |
| 0.0001 | 2.64792E+14 | 0.001133 | 2.441114 | 2.142857 | 2.325032753 | 0.116082 |
| 0.0002 | 2.68715E+14 | 0.001116 | 4.815166 | 4.285714 | 4.643585371 | 0.17158 |
| 0.0003 | 2.72638E+14 | 0.0011 | 7.128826 | 6.428571 | 6.949285437 | 0.179541 |
| 0.0004 | 2.76561E+14 | 0.001085 | 9.388072 | 8.571429 | 9.235971522 | 0.1521 |
| 0.0005 | 2.80484E+14 | 0.00107 | 11.59831 | 10.71429 | 11.49778794 | 0.100518 |
| 0.0006 | 2.84407E+14 | 0.001055 | 13.76446 | 12.85714 | 13.72926746 | 0.035193 |
| 0.0007 | 2.8833E+14 | 0.00104 | 15.89108 | 15 | 15.92539946 | 0.034317 |
| 0.0008 | 2.92252E+14 | 0.001027 | 17.9824 | 17.14286 | 18.0816818 | 0.099282 |
| 0.0009 | 2.96175E+14 | 0.001013 | 20.04239 | 19.28571 | 20.19415586 | 0.151769 |
| 0.001 | 3.00098E+14 | 0.001 | 22.07482 | 21.42857 | 22.25942503 | 0.184608 |
| 0.0011 | 3.04021E+14 | 0.000987 | 24.08331 | 23.57143 | 24.27465782 | 0.191349 |
| 0.0012 | 3.07944E+14 | 0.000974 | 26.07137 | 25.71429 | 26.23757732 | 0.166203 |
| 0.0013 | 3.11867E+14 | 0.000962 | 28.04246 | 27.85714 | 28.1464391 | 0.103977 |
| 0.0014 | 3.15789E+14 | 0.00095 | 30 | 30 | 30 | 0 |

FIG.17

| FREQUENCY LINEARITY | RESOLUTION (AT DEPTH OF 0.1mm) | RESOLUTION (AT DEPTH OF 1.0mm) |
|---|---|---|
| 0% | 9μm | 10μm |
| 0.1% | 9μm | 11μm |
| 0.3% | 9μm | 17μm |
| 0.5% | 9μm | 22μm |
| 0.7% | 9μm | 27μm |
| 4.7% | 22μm | NOT SMALLER THAN 100μm |

WAVELENGTH TUNABLE LASER AND OPTICAL TOMOGRAPHY SYSTEM USING THE WAVELENGTH TUNABLE LASER

BACKGROUND OF THE INVENTION

1. Field of the Invention

This invention relates to a wavelength tunable laser in which the oscillation wavelength is variable and an optical tomography system which obtains a tomographic image of the object to be measured by the use of the wavelength tunable laser.

2. Description of the Related Art

As a wavelength tunable laser whose oscillation wavelength is tunable, there has been known, for instance, an external resonator type laser shown in FIG. 12. (See U.S. Patent Application Publication No. 20050035295) In the laser shown in FIG. 12, light emitted from a low reflection face of a laser medium 111 is made parallel by a collimator lens 112 and then caused to enter a diffractive optics 113. The diffractive light which is spatially dispersed by the wavelength by the diffractive optics 113 is caused to enter a polygon mirror 125 by way of a pair of lenses 124a and 124b. Out of diffractive light which undergoes the wavelength dispersion by the diffractive optics 113, only components of a specific wavelength and those close thereto which are perpendicular to the reflecting surface of the polygon mirror 125 form return light and return to the semiconductor laser medium 111. The semiconductor laser medium 111 makes standing waves and emits light of the specific wavelength (to be referred to as "oscillating wavelength" hereinbelow. By rotating the polygon mirror 125, the wavelength of the return light can be continuously changed, whereby the oscillating wavelength can be swept. In the system shown in FIG. 12, the wavelength changes with time in proportion to $\sin \theta$ ($\theta$ is an inclination angle to the optical axis). Further, in U.S. Patent Application Publication No. 20050035295, there is disclosed a wavelength tunable laser, where a lens 134 and a rotary disk 135 are substituted for the lenses 124a and 124b and the polygon mirror 125 shown in FIG. 12 as shown in FIG. 13. In the laser, only light of a particular wavelength returns to the semiconductor laser medium 111 by virtue of the slit-like mirrors 135a which are disposed on the surface of the rotary disk 135 to diametrically linearly extend. By rotating the rotary disk 135, the wavelength of the light returning to the semiconductor laser medium 111 can be continuously changed, whereby the oscillating wavelength can be swept. In the system shown in FIG. 13, the wavelength changes with time in proportion to $\tan \theta$ ($\theta$ is rotating angle of the rotary disk 135), and substantially linearly changes.

In "Amplified, frequency swept lasers for frequency domain reflectometry and OCT imaging: design and scaling principles", R. Huber et al., OPTICS EXPRESS, Vol. 13, No. 9, pp. 3513-3528, 2005 there is further disclosed, as another system, a laser in which a tunable Fabry-Perot filter 143 is employed to select the oscillating wavelength in a fiber-ring resonator where an optical fiber 142 is connected to a semiconductor optical amplifier 141 at its opposite ends. In this system, the direction in which light passes is limited by a pair of isolators 144 and 145, and a laser beam is externally output from an optical coupler 146 provided in a part of the fiber-ring. In the system shown in FIG. 14, the wavelength changes with time is like a sine-wave by virtue of the characteristics of the tunable Fabry-Perot filter.

As an important application of the laser where the wavelength can be swept, there has been known an optical tomography system employing an SS-OCT (swept-source OCT) measurement. In the optical tomography system, coherence light emitted from a light source is divided into measuring light and reference light and the reflected light when the measuring light is projected onto the object and the reference light is multiplexed, whereby a tomographic image is obtained on the basis of the intensity of the interference light. In the SS-OCT optical tomography system, the interference light is detected while the frequency of the light emitted from the light source is changed with time, and the reflected light and the reference light are caused to interfere with each other while the frequency of the laser beam emitted from the light source is changed with time by the use of a Michelson interferometer. Then reflection intensity in a predetermined position in the direction of depth of the object is detected on the basis of the interferogram in the region of an optical frequency, and a tomographic image is generated by the use of the reflection intensity.

On the other hand, such an optical tomography system is applied to an endoscope and is employed in determinate diagnosis in a living body, a diagnosis of the depth of the cancer such as distinguishment between mucous membrane cancer (m cancer) and sub-mucous cancer (sm cancer), or the like. Procedure of cancer diagnosis under an endoscope will be briefly described, hereinbelow. First, a diseased part is found on the basis of a normal observing image, and the diseased part is distinguished whether it is a cancer. This primary diagnosis is based on experience of the doctor and whether the part is a cancer is determined by way of a pathology examination on the tissue of the part to be diagnosed as a cancer. Accordingly, determinate diagnosis during the examination through the endoscope is difficult under the present situation. When a human is diagnosed as having cancer, the depth of the cancer is examined again through an endoscope in order to determine a course of treatment. Generally, cancer is generated from the surface of a mucous membrane and infiltrates into a direction of depth while laterally expanding in response to progression thereof.

As shown in FIG. 15, the stomach wall comprises 5 layers, a mucous membrane layer (m layer), a mucous myotome (MM), a sub-mucous layer (sm layer), a muscular layer and a serous membrane layer. Cancer which stays a mucous membrane layer is called m cancer, while cancer which filtrates to the sub-mucous layer is called sm cancer. m cancer and sm cancer are different in the method of treatment. In the case of sm cancer since the lymphoid systems and/or the blood vessel systems exist in a sub-mucous layer and a probability of metastasis cannot be denied, a surgical operation is applied. On the other hand, in the case of m cancer, since a probability of metastasis is null, the cancer is extracted under an endoscope. Accordingly, it is important to distinguish the m cancer and the sm cancer. Specifically it is important for the image to be able to be evaluated whether the mucous myotome (MM layer) holds a layer structure or has been broken. At present, application of ultrasonic sound is investigated having in view on the diagnosis of the depth of the cancer. However, since the axial direction resolution is about 100 μm or so and imaging of the MM layer is insufficient, there is a demand for putting into practice a method of the optical tomography where the axial direction resolution at a depth of 1 mm is not larger than 30 μm.

In an optical tomography system using SS-OCT (swept source OCT) measurement, the axial direction resolution at a depth of 0 mm is governed by the sweeping wavelength band width and the central wavelength of the wavelength sweeping of the measuring light. Widening the measuring light sweeping wavelength band width has been progressed. As a result, an axial direction resolution of 10 μm or so can be obtained at a depth of 0 mm at the present.

However, in the wavelength tunable lasers shown in FIGS. 12 to 14, the wavelength change with time depicts a sin θ curve (θ representing the inclination angle from the optical axis) or a curve like a sine curve. In the above described optical tomography systems using SS-OCT (swept source OCT) measurement, there is often carried out on obtained data frequency analysis by the use of Fourier-transform and what is used as a variable when frequency analysis is carried out on obtained data by the use of Fourier-transform is not a wavelength but a frequency. There has been known that the axial direction resolution deteriorates as the measuring depth increases when data discretely distribute with respect to the variable in the analysis.

FIG. 16 shows a result of simulation where linearity of the frequency change with time of the measuring light and state of deterioration of the signal at a depth of 1 mm are calculated in such an optical tomography system. The linearity of the frequency change with time (sometimes referred to as "linearity of the frequency change", hereinbelow) is in terms of % while the difference between 0° and the real measured value of 30° when the polygon mirror 125 is rotated by 30° in the system shown in FIG. 12 is taken as a denominator and a maximum value of the part where the frequency change with time deviates from an ideal linear line when the polygon mirror 125 is rotated by 30° in the system shown in FIG. 12 is taken as a numerator. Further, when the wavelength change with time is linear, linearity of the frequency change is 4.7%.

As can be seen from FIG. 16, when the wavelength change with time of the measuring light is linear, that is, when the linearity of the frequency change with time of the measuring light is 4.7%, the deterioration of the signal at a depth of 1 mm and it is difficult to obtain an optical tomographic image by the use of such measuring light.

SUMMARY OF THE INVENTION

In view of the foregoing observations and description, the primary object of the present invention is to provide a wavelength tunable laser where the frequency change with time is linear, and to provide an optical tomography system which is provided with such a wavelength tunable laser.

The wavelength tunable laser of the present invention is an external resonator type wavelength tunable laser. In accordance with the present invention, there is provided a first external resonator type wavelength tunable laser comprising a laser medium, a dispersion means which spatially disperses light emitted from the laser medium by wavelength, and a wavelength selecting means having a reflecting surface which moves across the light which undergoes the wavelength dispersion by the dispersion means, and selectively reflects a part of the light which is reflected by the reflecting surface as a return light, the wavelength selecting means being structured so that the inverse of a number of a wavelength of the return light linearly changes with time.

As the dispersion element, for instance, a diffractive optics, prism or grism may be employed. The expression "the inverse of a number of a wavelength of the return light linearly changes with time" is of a same meaning as the expression "the frequency of the return light linearly changes with time" and the expression "the wave number of the return light linearly changes with time". This is derived from the fact that the relation between the wavelength λ, the frequency ν, the wave number k and the velocity c of light is ν=c/λ, k=2π/λ. Further, when the wavelength sweeping is repeated at predetermined periods in the first wavelength tunable laser of the present invention, it is assumed that the inverse of a number of a wavelength linearly changes with time for the changes in the period. The inverse of a number of a wavelength of the return light need not strictly linearly changes with time but may substantially linearly changes with time.

In the above described wavelength tunable laser, the reflecting surface may be partially formed in a body of rotation rotatable about a predetermined axis to extend substantially in a diametrical direction of the body of rotation like a curve to be concave toward the forward of the direction of rotation of the body of rotation.

Further, the first wavelength tunable laser of the present invention may be formed so that lights dispersed by the wavelength by the dispersion means in a plane which includes the reflecting surface and is perpendicular to the predetermined axis are disposed on a linear line in a direction intersecting a diametrical direction of a body of rotation and the distances from the light of the wavelengths to the predetermined axis are simply decreased or increased.

Further, in accordance with the present invention there is provided a first optical tomography system comprising the above wavelength tunable laser. The first optical tomography system of the present invention comprises the wavelength tunable laser defined in any one of Claims 1 to 3, a light dividing means which divides the light emitted from the wavelength tunable laser into measuring light and reference light, a multiplexing means which multiplexes the reflected light from the object when the measuring light is projected onto the object and the reference light, an interference light detecting means which detects interference light of the reflected light and the reference light which have been multiplexed by the multiplexing means, and a tomographic image obtaining means which obtains a tomographic image of the object on the basis of the interference light detected by the interference light detecting means.

In accordance with the present invention, there is provided a second external resonator type wavelength tunable laser comprising a laser medium, a dispersion means which spatially disperses light emitted from the laser medium by wavelength, a rotating polygon mirror which selectively reflects a part of the light which is dispersed by wavelength by the dispersion means as a return light, and a distortion generating means disposed between the dispersion means and the rotating polygon mirror, the distortion generating means generating a distortion so that the inverse of a number of a wavelength of the return light substantially linearly changes with time.

As the dispersion element, for instance, a diffractive optics, prism or grism may be employed. The expression "the inverse of a number of a wavelength of the return light linearly changes with time" is of a same meaning as the expression "the frequency of the return light linearly changes with time" and the expression "the wave number of the return light linearly changes with time". This is derived from the fact that the relation between the wavelength λ, the frequency ν, the wave number k and the velocity c of light is ν=c/λ, k=2π/λ. Further, when the wavelength sweeping is repeated at predetermined periods in the wavelength tunable laser of the present invention, it is assumed that the inverse of a number of a wavelength linearly changes with time for the changes in the period. The inverse of a number of a wavelength of the return light need not strictly linearly changes with time but may substantially linearly changes with time.

In the above described wavelength tunable laser, when a lens group comprising at least two lenses is disposed between the dispersion means and the rotating polygon mirror, the lens group may double as the distortion generating means.

The lens group may comprise a pair of lenses, one being $F(\theta)=f\cdot\sin\theta$ in a distortion curve, the other being $G(\theta)=f\cdot\tan\theta$ in a distortion curve. Further, the lens group may comprise lenses where correction has been made on the lenses of $F(\theta)=f\cdot\sin\theta$, and $G(\theta)=f\cdot\tan\theta$ to approach an ideal distortion characteristics where the inverse of a number of a wavelength of the return light perfectly linearly changes with time. f represents a focal length and θ represents an angle of view.

The distortion generating means may generate a distortion where the inverse of a number of a wavelength of the return light gives a linearity of not larger than 0.7% to time within a predetermined rotating angle of the rotating polygon mirror.

The linearity of not larger than 0.7% means that the % obtained with the difference between the real measured values of maximum and minimum rotating angles of the rotating polygon mirror taken as a denominator and a maximum value of the differences between the real measured value and an ideal linear line taken as a numerator is not larger than 0.7% within a predetermined rotating angle of the rotating polygon mirror. The predetermined angle may be 30°.

In accordance with the present invention, there is provided a second optical tomography system comprising
  a wavelength tunable laser,
  a light dividing means which divides the light emitted from the wavelength tunable laser into measuring light and reference light,
  a multiplexing means which multiplexes the reflected light from the object when the measuring light is projected onto the object and the reference light,
  an interference light detecting means which detects interference light of the reflected light and the reference light which have been multiplexed by the multiplexing means, and
  a tomographic image obtaining means which obtains a tomographic image of the object on the basis of the interference light detected by the interference light detecting means.

In accordance with the first wavelength tunable laser of the present invention, since a part of light dispersed by the dispersion means selectively returns to the laser medium as return light and light having a wavelength of the return light as an oscillating wavelength is emitted from the first wavelength tunable laser of the present invention. Since the wavelength selecting means being structured so that the inverse of a number of a wavelength of the return light linearly changes with time, a wavelength tunable laser where the frequency of emitted light linearly changes with time can be obtained.

When the reflecting surface is partially formed in a body of rotation rotatable about a predetermined axis to extend substantially in a diametrical direction of the body of rotation, the reflecting surface moves across the light which has been dispersed by wavelength by the dispersion means in response to rotation of the body of rotation by opposing the reflecting surface to the light which has been dispersed by wavelength by the dispersion means, whereby a structure where a part of the light is selectively reflected can be easily obtained. Further, when the reflecting surface is like a curve to be concave toward the forward of the direction of rotation of the body of rotation, the system is different from that shown in FIG. 9, where the wavelength change with time is like sine, and the frequency of the return light can be linearly changed with time by suitably setting the shape of the curve.

Further, in the above described structure, when lights dispersed by the wavelength by the dispersion means is positioned in perpendicular to the predetermined axis on a linear line in a direction intersecting a diametrical direction of a body of rotation on a plane which includes the reflecting surface and the distances from the light of the wavelengths to the predetermined axis are simply decreased or increased, since the points which reflects the light on the reflecting surface extending substantially a diametrical direction of a body of rotation satisfy a relation of a one-to-one correspondence with the wavelengths of the return light, the shape of the reflecting surface can be designed so that the inverse of a number of the wavelength of the return light is linearly changed with time by taking the coordinates of each point and the wavelength of the return light as the variables.

In accordance with the first tomography system of the present invention, since a tomographic image is obtained by the use of light emitted from the above described wavelength tunable laser, the frequency of the measuring light linearly changes with time. Accordingly, it is easy to obtain data so that the data distribution with respect to the frequency is substantially uniformly spaced and a good result can be obtained in the frequency analysis upon obtaining a tomographic image.

Since the second wavelength tunable laser in accordance with the present invention comprises
  a laser medium,
  a dispersion means which spatially disperses light emitted from the laser medium by wavelength,
  a rotating polygon mirror which selectively reflects a part of the light which is dispersed by wavelength by the dispersion means as return light, and
  a distortion generating means disposed between the dispersion means and the rotating polygon mirror,
  the distortion generating means generating a distortion so that the inverse of a number of a wavelength of the return light substantially linearly changes with time,
  there can be obtained a laser in which the frequency of the light emitted therefrom is linearly changed with time.

Further, when a lens group comprising at least two lenses is disposed between the dispersion means and the rotating polygon mirror and the lens group doubles as the distortion generating means, the emitted light can be linearly changed with time without adding to the size of the wavelength tunable laser.

When the lens group comprises a pair of lenses, one being $F(\theta)=f\cdot\sin\theta$ in a distortion curve, the other being $G(\theta)=f\cdot\tan\theta$ in a distortion curve, aberrations other than the distortion can be easily removed. Further, by correcting the lenses, a more ideal distortion curve can be obtained.

Since the second optical tomography system of the present invention obtains a tomographic image by the use of light emitted from the above described second wavelength tunable laser, the frequency of the measuring light substantially linearly changes with time. Accordingly, it is easy to obtain data so that the data distribution with respect to the frequency is substantially uniformly spaced and a good result can be obtained in the frequency analysis upon obtaining a tomographic image.

As can be seen from FIG. 16, the signal substantially deteriorates when the linearity of the frequency change with time of the measuring light exceeds 0.7%. FIG. 17 shows a result of simulation where when an optical tomographic image is obtained by the use of low coherence light of Gaussian distribution which is 1150 nm in the central wavelength and 200 nm in the wavelength width, the relation between the linearity of the frequency change and the axial resolution (at depths of 0.1 mm and 1 mm) is simulated. As can be seen from FIG. 17, when the axial resolution of 10 μm or so can be obtained at depths of 0 mm so long as the linearity of the frequency change with time is not larger than 0.7%, the axial resolution of 30 μm can be realized at depths of 1 mm. That is, a system suitable for diagnosis of depth of cancer such as extraction of mucous myotome (MM) cancer under an endoscope can be realized by an optical tomography system by the use of a wavelength tunable laser provided with a distortion generating means in which the inverse of a number of a wavelength of the return light gives to time a linearity of not larger 0.7% within a predetermined rotating angle of the rotating polygon mirror, e.g. 30°.

BRIEF DESCRIPTION OF THE DRAWINGS

FIG. 4 is a view showing an example of the calculation in this embodiment, FIG. 6 is a view showing the wavelength selecting means of the conventional systems, FIGS. 7A and 7B are views showing the wavelength selecting means of modifications of the laser of the present invention, FIG. 10 is a view showing the relation between the distortion curve and the oscillating frequency in the laser shown in FIG. 8, FIG. 17 is a view illustrating the relation between the linearity of the frequency change with time and the axial resolution when an optical tomographic image is to be obtained at the depth of 1 mm.

DESCRIPTION OF THE PREFERRED EMBODIMENT

Figure 1:
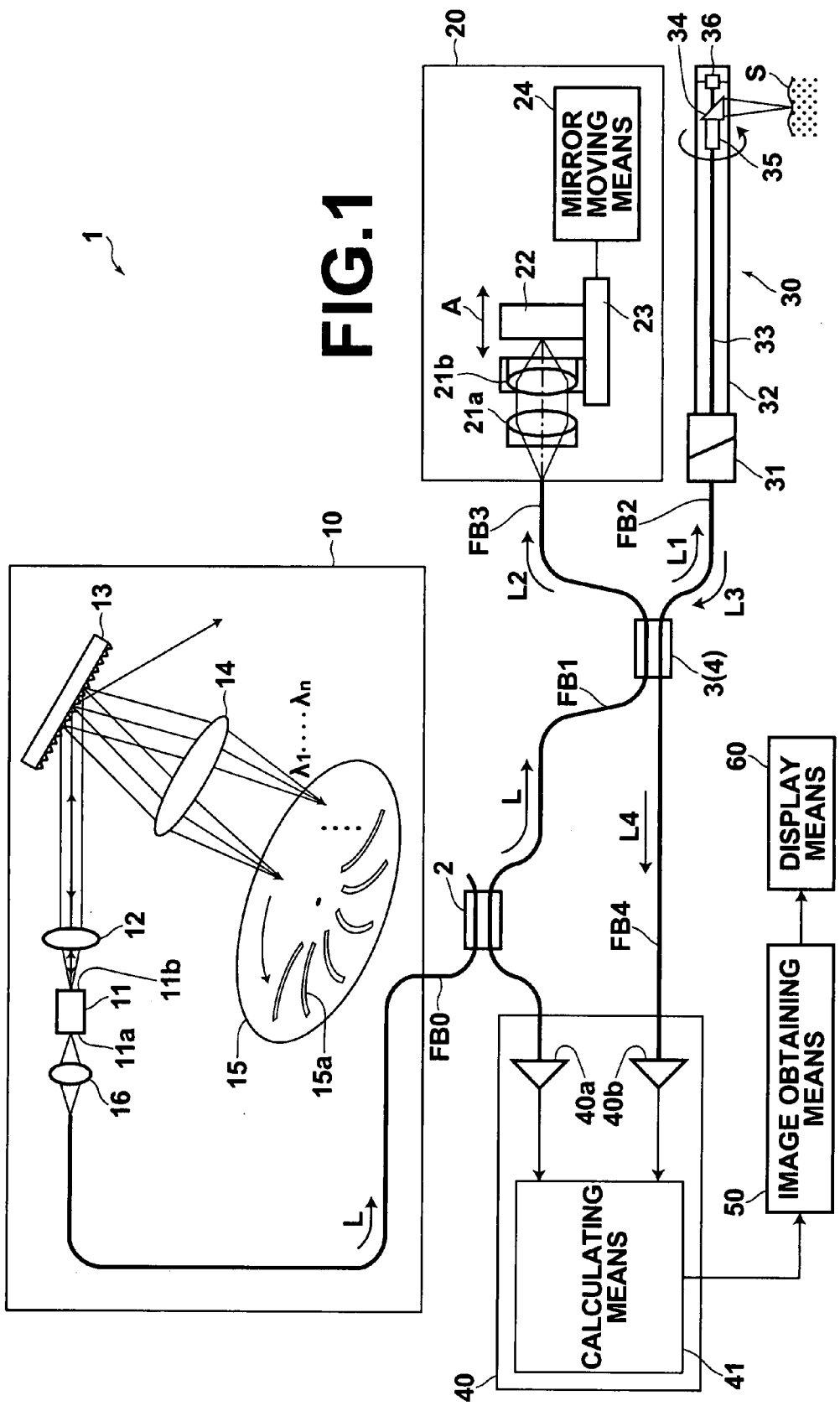
FIG. 1 is a view showing in brief an optical tomography system in accordance with a first embodiment of the present invention.

Embodiments of a wavelength tunable laser of the present invention and an optical tomography system provided with the wavelength tunable laser will be described in detail with reference to the drawings, hereinbelow. FIG. 1 is a schematic diagram that illustrates an optical tomography system in accordance with an embodiment of the present invention. The optical tomography system 1 of this embodiment is for obtaining a tomographic image of an object of measurement such as a living tissue or a cell in a body cavity by measuring the SS-OCT. The optical tomography system 1 of this embodiment comprises: a laser 10 which emits light L while sweeping the oscillating wavelength at predetermined periods; a light dividing means 3 which divides the light L emitted from the laser 10 into measuring light beam L1 and reference light beam L2; an optical path length adjusting means 20 which adjusts the optical path length of the reference light beam L2 divided by the light dividing means; a probe 30 which guides to the object S to be measured the measuring light beam L1 divided by the light dividing means 3; a multiplexing means 4 for multiplexing a reflected light beam L3 from the object S when the measuring light beam L1 is irradiated onto the object S from the probe 30, and the reference light beam L2; an interference light detecting means 40 for detecting interference light beam L4 of the reflected light beam L3 and the reference light beam L2 which have been multiplexed by the multiplexing means 4; and an image obtaining means 50 which obtains a tomographic image of the object S by carrying out frequency-analysis on the interference light L4 detected by the interference light detecting means 40.

The laser 10 is an external resonator type wavelength tunable laser which emits a laser beam L while sweeping the oscillating wavelength. In this particular embodiment, a semiconductor laser medium employed in semiconductor lasers is employed as the laser medium. Specifically, the laser 10 comprises a semiconductor laser medium 11, a collimating lens 12, a diffractive optics 13, a collecting lens 14 and a rotational body (body of rotation) 15. An antireflection coating (AR coating) is provided on the light emitting end face 11b of the semiconductor laser medium 11 facing the collimating lens 12. A lens 16 for an optical coupling is disposed between the light emitting end face 11a of the semiconductor laser medium 11 opposite to the light emitting end face 11b and an optical fiber FB0 for externally guiding the wave.

The diffractive optics 13 is a reflection type element and functions as a dispersion element which disperses emitted light from the laser medium 11 by the wavelength. The diffractive light generated by the diffractive optics 13 travels toward the directions different by the wavelengths.

The rotational body 15 comprises a disk which is opposed to the collecting lens 14 and is provided with a plurality of reflecting surfaces 15a and functions as the wavelength selecting means of the present invention. The rotational body 15 is substantially in the form of a disk rotating at a constant angular velocity about a predetermined axis by a drive means (not shown). The surface of the rotational body 15 opposed to the collecting lens 14 is partially provided with a plurality of reflecting surfaces 15a each of which reflects light. The reflecting surfaces 15a extend substantially in a diametrical direction of the rotational body 15, and are like a curve to be concave toward the forward of the direction of rotation of the rotational body 15. The structure of the reflecting surface 15a will be described in detail later. In FIG. 1, the reference numeral 15a is attached to only one of the reflecting surfaces and a part of the reflecting surfaces are abbreviated for the purpose of simplicity.

The part of the surface of the rotational body 15 other than the reflecting surfaces 15a is provided with a non-reflection coating. Specifically the part of the surface of the rotational body 15 other than the reflecting surfaces 15a is treated with, for instance, a dispersion treatment such as a black coating, an AR coating, or an etching/sand blast. By treating with such a dispersion treatment, noise components are reduced and the S/N ratio of the reflected light is improved, whereby oscillation (ripple) of light having a wavelength other than the desired wavelength can be suppressed. The non-reflection treatment can be applied to the conventional system shown in FIG. 9 where a rotary disk having a reflecting part and a non-reflecting part is employed.

Light emitted from the light emitting end face 11b of the semiconductor laser medium 11 is dispersed by the diffractive optics 13 by the wavelengths λ1 . . . λn after converted to parallel light by the collimating lens 12 and travels in different directions by the wavelengths. The light dispersed by the wavelengths is collected by the collecting lens 14 on the surface of the rotational body 15.

In response to rotation of the rotational body 15, the reflecting surfaces 15a move across the light which has been dispersed by the wavelength to selectively reflect a part of the light as the return light. The return light travels along the reverse optical path to return to the semiconductor laser medium 11 by way of the collecting lens 14, the diffractive optics 13 and the collimating lens 12. An external resonator having its opposite ends at the light emitting end face 11a of the semiconductor laser medium 11 and the rotational body 15 is thus formed and light L is emitted from the light emitting end face 11a of the semiconductor laser medium 11. The oscillating wavelength of this light L is the wavelength of the return light.

The wavelength of the return light changes in response to rotation of the rotational body 15, and the wavelength sweeping of one period, from λ1 to λn, is effected for each of the reflecting surfaces 15a. Since a plurality of the reflecting surfaces 15a are provided at predetermined intervals, the wavelength sweeping is repeated at constant periods.

Figure 2:
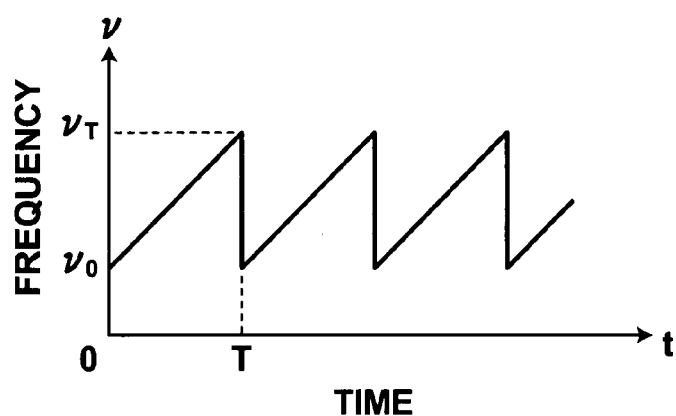
FIG. 2 is a view showing the wavelength sweep of the laser shown in FIG. 1.

The wavelength sweeping in the optical tomography system 1 is arranged so that the inverse of a number of the wavelength of the return light linearly changes with time. Since the wavelength λ, the frequency ν and the velocity of light c are in the relation of ν=c/λ, the wavelength sweeping in the optical tomography system 1 is arranged so that the frequency of the return light linearly changes with time, and the optical tomography system 1 after all sweeps the wavelength of the return light so that the frequency ν (t) of the return light linearly changes with time t during the sweeping time T corresponding to one period as shown in FIG. 2. In FIG. 2, the frequency of the return light at the sweeping initiating time (t=0) of each period is $\nu_o$, and the frequency of the return light at the sweeping ending time (t=T) of the period is $\nu_T$.

Figure 3:
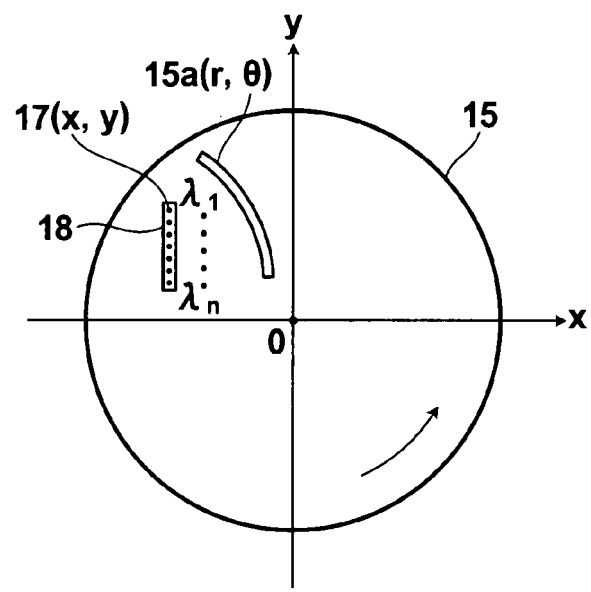
FIG. 3 is a view showing the wavelength selecting means of the laser shown in FIG. 1.

A method of designing the reflecting surface 15a which realizes the above described method of wavelength sweeping will be described with reference to FIG. 3 together with detail of the reflecting surface 15a. In a surface of the rotational body 15 which includes the reflecting surface 15a and is perpendicular to the rotational axis, it is assumed that the position of the rotational axis is the origin O, and two axes passing through the origin O in perpendicular to each other are x-axis and y-axis.

The reflecting surface 15a extends substantially in a diametrical direction of the rotational body 15 like an elongated curve to be concave toward the forward of the direction of rotation of the rotational body 15. The arrangement 18 of lights spatially dispersed by the wavelength by the diffractive optics 13 is positioned in the second quadrant (x<0, y>0) in parallel to y-axis in the order of θ1 . . . θn and the distances from the origin O to the lights of the respective wavelengths are simply decreased or increased in the order of the wavelengths.

Since a part of the arrangement 18 of lights forms the return light when the reflecting surface 15a intersects the arrangement 18 of lights spatially dispersed by the wavelength, the intersection of the reflecting surface 15a and the arrangement 18 of lights is a reflecting position 17 of the return light. Since the reflecting surface 15a moves in response to rotation of the rotational body 15, the position of the reflecting position 17 of the return light changes. The reflecting position 17 is obtained by continuously scanning the arrangement 18 of lights in the order of wavelengths, and the locus of the scan is the same of the arrangement 18 of lights. However, in FIG. 3, the reflecting position 17 is conceptually represented by sets of points in order to describe the reflecting position 17 and the arrangement 18 of lights as different concepts.

Though the reflecting position 17 and the arrangement 18 of lights are illustrated as having a predetermined width, they are not constantly in the full-scale. Since the arrangement 18 of lights is formed by lights obtained by collecting by the collecting lens 14 lights which is parallel light, it is equivalent to the beam waist diameter in the width. Further, in order to hold a high resolution of the sweeping wavelength, it is preferred that the width of the reflecting surface 15a be equivalent to the beam waist diameter.

The method of designing the reflecting surface 15a will be described with reference to formulae hereinbelow. Since the frequency ν(t) of the return light is proportional to time (t) in the tomography system 1 of this embodiment, the following formula is satisfied.

$$\nu(t)=\nu_0+(\nu_T-\nu_0)/(T \cdot t)$$

Then the x coordinate and the y coordinate of the reflecting position 17 of the return light are taken as a function of time t and are respectively represented by (x(t), y(t)). $x_0$, $y_0$ and $y_T$ are substituted for x(t), y(t) and y(T), that is, $x_0=x(t)$, $y_0=y(t)$ and $y_T=y(t)$. In order to correspond the reflecting position and the frequency of the return light in one-to-one correspondence to each other, y(t) is made to be in proportion to ν(t). At this time, the following formula is satisfied.

$$y(t)=Y_0-(y_T-y_0) \cdot (\nu(t)-\nu_0)/(\nu_T-\nu_0)$$

Under the above described conditions, (r, θ) coordinates of a position where the reflecting surface 15a reflects the return light are determined as a variable of time t. The (r, θ) coordinates represent a radius r and a rotational angle from y-axis which are expressed as follows by the use of the above x(t) and y(t) and the angular velocity α (in rad/sec) of the rotational body 15 when they are respectively represented by r(t) and θ(t).

$$r(t)=y(t)\cos \theta(t)$$

$$\theta(t)=\tan^{-1}(x_0/y(t))+\alpha \cdot t$$

When a plurality of, for instance, two, reflecting surfaces 15a are provided, r(t) and θ(t) are as follows.

$$r(t)=y(t)\cos \theta(t)$$

$$\theta_N(t)=\theta(t)+N \cdot \alpha \cdot t$$

Figure 5:
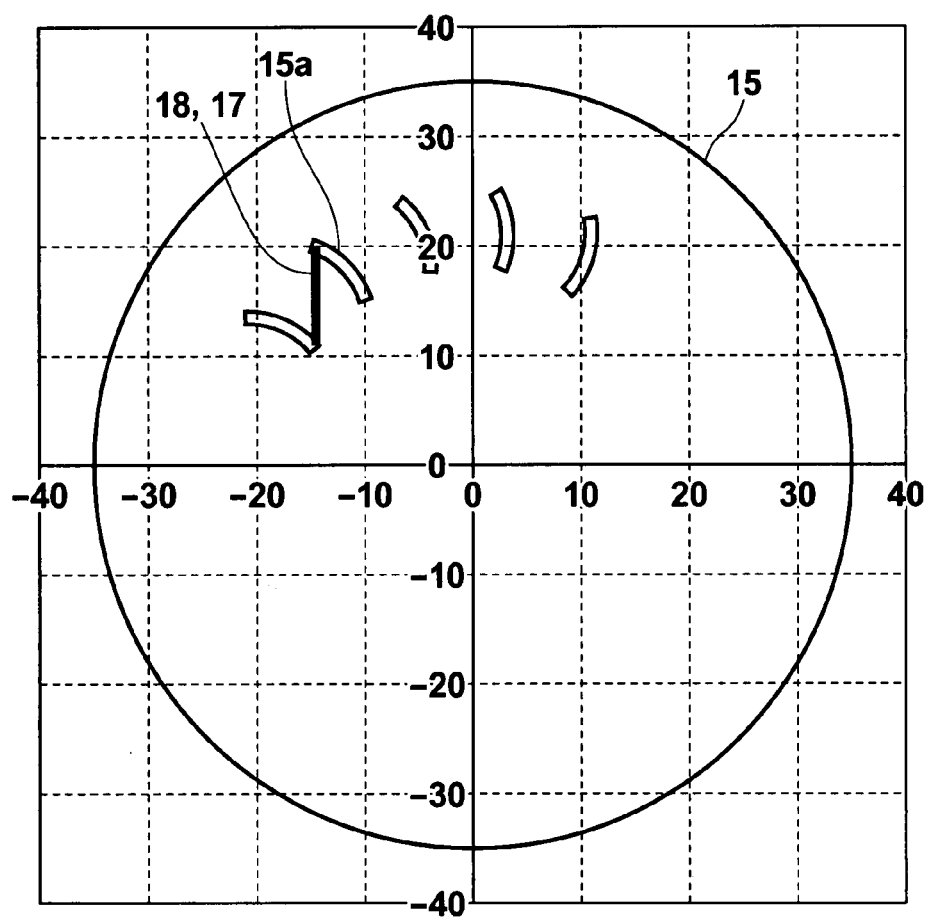
FIG. 5 is a view showing the relative positions of the elements such as the reflecting surface on the basis of the example of the calculation shown in FIG. 4.

An example of calculation based on the above formula is shown in FIG. 4. FIG. 4 shows values calculated for one reflecting surface 15a and the value of the parameter attached with a * in the table in FIG. 4 is an input value. Reflecting surfaces 15a, arrangements 18 of lights, and reflecting positions 17 which are obtained by similar calculation on a plurality of reflecting surfaces are shown in FIG. 5. In FIG. 5, the arrangement 18 of lights, and the reflecting positions 17 are superposed and are shown by the thick black line.

Figure 9:
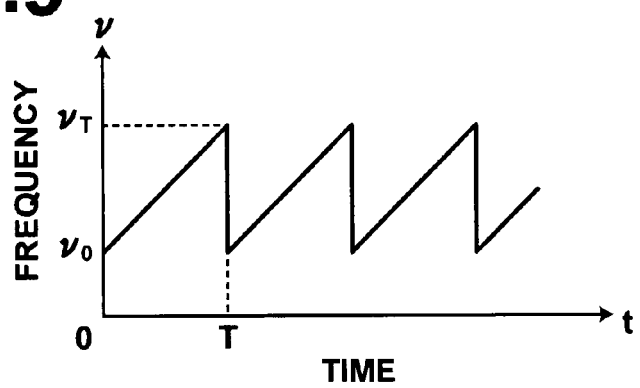
FIG. 9 is a view showing the wavelength sweep of the laser shown in FIG. 8.

FIG. 6 shows the reflecting surface 135a, the arrangement 116 of lights, and the reflecting positions 117 of the conventional system shown in FIG. 9. In FIG. 6, they are conceptually represented as in FIG. 3. As shown in FIG. 6, in the conventional system, the arrangement 116 of lights exists over the second and third quadrants, and the distances from the origin O to the lights of the respective wavelengths are not simply decreased or increased in the order of the wavelengths whereby the reflecting position and the frequency of the return light do not correspond to each other in one-to-one correspondence.

On the other hand, in the optical tomography system 1 of this embodiment, the arrangement 18 of lights is positioned in the second quadrant (x<0, y>0) in parallel to y-axis in the order of wavelengths and the distances from the origin O to the lights of the respective wavelengths are simply decreased or increased in the order of the wavelengths whereby the reflecting position and the frequency of the return light correspond to each other in one-to-one correspondence, and the reflecting surface can be designed so that the frequency of the return light linearly changes with time.

In this embodiment shown in FIG. 1, parallel light impinges upon the diffractive optics 13 and the collecting lens 14 is disposed so that the distance between the collecting lens 14 and the rotational body 15 is equal to the focal length of the collecting lens 14. Since the rotational body 15 is thus disposed in the focal plane of the collecting lens 14 on which light is collected by the collecting lens 14, the beam diameter on the rotational body 15 can be small. As the beam diameter is smaller, the reflecting surface 15a of the rotational body 15 can be smaller in width, and resolution of the wavelength swept by scanning of the reflecting surface 15a can be increased.

Further, in this embodiment, the distance between the collecting lens 14 and the diffractive optics 13 is equal to the focal length of the collecting lens 14 and the face of the collecting lens 14 facing the rotational body 14 is telecentric. Further, the reflecting surfaces 15a of the rotational body 15 are in perpendicular to the optical axis of the collecting lens 14. With this arrangement, the chief rays of light traveling from the collecting lens 14 to the rotational body 15 are parallel to the optical axis of the collecting lens 14 and perpendicular to the reflecting surfaces 15a of the rotational body 15 so that they return along the reverse optical path after reflected by the rotational body 15.

In the laser 10 which has been described above in detail, light L which is emitted from the light emitting end face 11a of the semiconductor laser medium 11 enters optical fiber FB0 to be guided thereby after being collected by the lens 16 for an optical coupling. The laser light L is then guided to the light dividing means 3 by an optical fiber FB1 by way of a fiber coupler 2.

The light dividing means 3 comprises, for instance, a 2×2 fiber optic coupler and divides the light L led thereto by way of the optical fibers FB0 and FB1 from the laser 10 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. The light dividing means 3 in this particular embodiment also functions as the multiplexing means 4.

The probe 30 is optically connected to the optical fiber FB2 and the measuring light beam L1 is guided to the probe 30 from the optical fiber FB2. The probe 30 is inserted into a body cavity, for instance, through a forceps port by way of a forceps channel and is removably mounted on the optical fiber FB2 by an optical connector 31.

The optical probe 30 comprises a cylindrical outer envelope 32 closed at the leading end thereof, an optical fiber 33 which is disposed inside the outer envelope 32 to extend along the axis of the outer envelope 32, a prism mirror 34 which deflects light L1 radiated from the leading end portion of the optical fiber 33 in a circumferential direction of the outer envelope 32, a rod lens 35 which converges light L1 radiated from the leading end portion of the optical fiber 33 on an object S to be measured as a body to be scanned which is disposed in the outer part in the circumference of the outer envelope 32 and a motor 36 which rotates the prism mirror 34 about the axis of the optical fiber 33.

The optical path length adjusting means 20 is disposed on the side of the optical fiber FB3 radiating the reference light beam L2. The optical path length adjusting means 20 changes the optical path length of the reference light beam L2 in order to adjust the position from which a tomographic image is initiated to be obtained and comprises a reflecting mirror 22 which reflects the reference light beam L2 radiated from the optical fiber FB3, a first lens 21a disposed between the reflecting mirror 22 and the optical fiber FB3, and a second lens 21b disposed between the first lens 21a and the reflecting mirror 22.

The first lens 21a makes parallel the reference light beam L2 radiated from the core of the optical fiber FB3 and at the same time, collects the reference light beam L2 reflected by the reflecting mirror 2 on the core of the optical fiber FB3. The second lens 21b collects the reference light beam L2 made parallel by the first lens 21a on the reflecting mirror 22 and at the same time, makes parallel the reference light beam L2 reflected by the reflecting mirror 22.

Accordingly, the reference light beam L2 radiated from the optical fiber FB3 is turned to a parallel light by the first lens 21a and is collected on the reflecting mirror 22 by the second lens 21b. Subsequently, the reference light beam L2 reflected by the reflecting mirror 22 is turned to a parallel light by the second lens 21b and is collected on the core of the optical fiber FB3 by the first lens 21a.

The optical path length adjusting means 20 is further provided with a movable stage 23 to which the second lens 21b and the reflecting mirror 22 are fixed and a mirror movement means 24 which moves the movable stage 23 in the direction of the optical axis of the first lens 21a. In response to movement of the movable stage 23 in the direction of arrow A, the optical path length of the reference light beam L2 can be changed.

The multiplexing means 4 comprises a 2×2 fiber optic coupler as described above, and multiplexes the reference light beam L2 which has been changed in its optical path length by the optical path length adjusting means 20 and the reflected light beam L3 from the object S to emit the multiplexed light beam toward the interference light detecting means 40 by way of an optical fiber FB4.

The interference light detecting means 40 detects interference light L4 of the reflected light beam L3 and the reference light beam L2 which have been multiplexed by the multiplexing means. Further, in this particular embodiment, the interference light detecting means 40 guides lights obtained by dividing the interference light L4 into two by the light dividing means 3 which is a fiber coupler to an optical detectors 40a and 40b and a balanced detection is carried out in a calculating means 41.

The calculating means 41 is connected to an image obtaining means 50 comprising, for instance, a computer system such as a personal computer. The image obtaining means 50 is connected to a display system 60 formed, for instance, by a CRT or a liquid crystal display system. The image obtaining means 50 obtains intensity of the reflected light beam L3 in each of the positions in the direction of depth of the object S by carrying out frequency analysis by Fourier-transform on the interference light L4 detected by the interference light detecting means 40 and obtains a tomographic image of the object S. The tomographic images thus obtained are displayed by the display system 60.

Here, detection of the interference light beam L4 in the interference light detecting means 40 and image generation in the image obtaining means 50 will be described briefly. Note that a detailed description of these two points can be found in M. Takeda, "Optical Frequency Scanning Interference Microscopes", Optics Engineering Contact, Vol. 41, No. 7, pp. 426-432, 2003.

When the measuring light beam L1 is projected onto the object Sb, the reflected light L3 from each depth of the object Sb and the reference light L2 interfere with each other with various optical path length difference l. When the light intensity of the interference fringe at this time versus each optical path length difference l is assumed to be S(l), the light intensity I(k) detected in the interference light detecting means 40 is expressed by the following formula.

$$I(k)=\int_0^\infty S(l)[1+\cos(kl)]dl \quad (1)$$

wherein k represents the wave number and l represents the optical path length difference. Formula (1) may be considered to be given as an interferogram of a light frequency range having a wave number k as a variable. Accordingly, a tomographic image is generated by obtaining in the image obtaining means 50 information on the distance of the object S from the measurement initiating position and information on the intensity of reflection by carrying out frequency analysis by Fourier-transform on the spectral interference fringes detected by the interference light detecting means 40 and determining the intensity S(l) of the interference light beam L4.

Operation of the optical tomography system 1 having a structure described above will be described, hereinbelow. When a tomographic image is to be obtained, the optical path length is first adjusted by moving the movable stage 23 in the direction of the arrow A so that the object S is positioned in the measurable area. The laser light L is subsequently emitted from the laser 10 and the laser light L is divided into the measuring light beam L1 and the reference light beam L2 by the dividing means 3. The measuring light beam L1 is led by the optical probe 30 into a body cavity and is projected onto the object S. The reflected light beam L3 from the object S and the reference light beam L2 reflected by the reflecting mirror 22 are multiplexed by the multiplexing means 4 and the interference light beam L4 of the reflected light beam L3 and the reference light beam L2 is detected by the interference light detecting means 40. A tomographic image is obtained by carrying out frequency analysis on a signal of the detected interference light beam L4 in the image obtaining means 50.

By rotating the probe 30 so that the measuring light beam L1 scans the object S in a one-dimensional direction, information on the direction of depth of the object S is obtained in each part along the direction of scan and accordingly tomographic images on the cross-section including the direction of scan can be obtained. Further, by moving the measuring light L1 with respect to the object S to scan in a second direction perpendicular to said direction of scan, tomographic images on the cross-section including the second direction can be obtained.

In the tomography system 1 of this embodiment described above, since the system is arranged so that the frequency of light generated therefrom linearly changes with time, data can be easily obtained so that the data distribution cannot be discrete and the data distribution with respect to the frequency is uniformly spaced, whereby the accuracy in the frequency-analysis can be improved as compared with the conventional. For example, there has been reported that when a tomographic image signal of an object which is 2 mm in depth is to be detected, a linearity of frequency change with time should be at least 0.1%. The tomography system 1 of this embodiment can easily satisfy this condition.

The layout of the arrangement of lights and/or arrangement and layout of the reflecting surface such as the shape of the reflecting surface need not be limited to those shown in the above embodiment or in FIG. 5 but various modifications are conceivable. For example, in the system where the arrangements of lights 216 are disposed on the surface of the rotational body 215 in the order in which the absolute values of the x-coordinates increase as shown in FIG. 7A, the angle between the arrangement of lights 216 and the reflecting surface 215a approaches to 90° and the return light becomes narrow in the wavelength width, whereby the sweeping wavelength resolution can be higher. However, a note should be taken that when the absolute values of the x-coordinates are too large, the length of the arrangement of lights 216 in the y-direction becomes insufficient and the wavelength resolution in the arrangement of lights 216 can deteriorate. Further, in this case, since the curvature of the reflecting surface 215a becomes sharp, it is necessary to largely space adjacent reflecting surfaces 215a. As a result, the sweeping period is elongated, the sweeping speed deteriorates and the number of reflecting surfaces which can be provided on the surface of the rotational body is reduced.

On the other hand, in the system where the arrangements of lights 316 are disposed on the surface of the rotational body 315 in the order in which the absolute values of the x-coordinates decrease as shown in FIG. 7B, the curvature of the reflecting surface 315a becomes gentle and the angle between the arrangement of lights 316 and the reflecting surface 315a is minimized, whereby the sweeping speed and the number of reflecting surfaces which can be provided on the surface of the rotational body is increased though the sweeping wavelength resolution deteriorate. It is preferred that the layout of the arrangement of lights and/or arrangement and layout of the reflecting surface be determined according to the specification which the wavelength tunable laser or the optical tomography system is required to satisfy.

Figure 8:
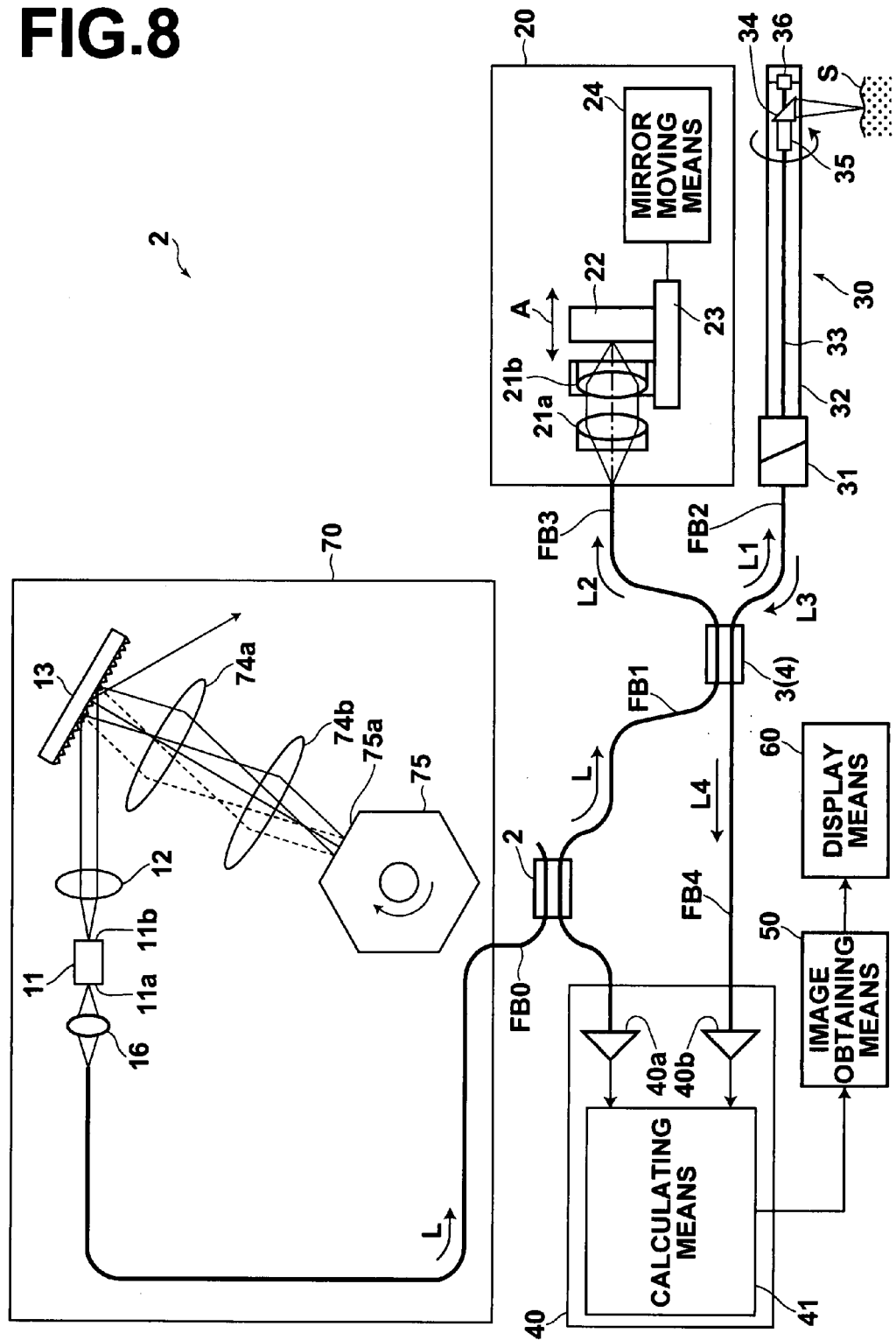
FIG. 8 is a view showing in brief an optical tomography system in accordance with a second embodiment of the present invention.

An optical tomography system 2 in accordance with a second embodiment of the present invention will be described, hereinbelow, with reference to FIG. 8. FIG. 8 is a view that illustrates the optical tomography system 2. In the optical tomography system 2 shown in FIG. 8, elements analogous to those in the optical tomography system 1 shown in FIG. 1 are given the same reference numerals and will not be described.

The optical tomography system 2 of this embodiment is for obtaining a tomographic image of an object of measurement such as a living tissue or a cell in a body cavity by measuring the aforesaid SS-OCT. The optical tomography system 2 of this embodiment comprises: a laser 70 which emits light L while sweeping the oscillating wavelength at predetermined periods; a light dividing means 3 which divides the light L emitted from the laser 70 into measuring light beam L1 and reference light beam L2; an optical path length adjusting means 20 which adjusts the optical path length of the reference light beam L2 divided by the light dividing means; a probe 30 which guides to the object S to be measured the measuring light beam L1 divided by the light dividing means 3; a multiplexing means 4 for multiplexing a reflected light beam L3 from the object S when the measuring light beam L1 is irradiated onto the object S from the probe 30, and the reference light beam L2; an interference light detecting means 40 for detecting interference light beam L4 of the reflected light beam L3 and the reference light beam L2 which have been multiplexed by the multiplexing means 4; and an image obtaining means 50 which obtains a tomographic image of the object S by carrying out frequency-analysis on the interference light L4 detected by the interference light detecting means 40.

The laser 70 is an external resonator type wavelength tunable laser which emits a laser beam L while sweeping the oscillating wavelength. In this particular embodiment, a semiconductor laser medium employed in semiconductor lasers is employed as the laser medium. Specifically, the laser 70 comprises a semiconductor laser medium 11, a collimating lens 12, a diffractive optics 13, a pair of lenses 74a and 74b and a polygon mirror 75. An antireflection coating (AR coating) is provided on the light emitting end face 11b of the semiconductor laser medium 11 facing the collimating lens 12. A lens 16 for an optical coupling is disposed between the light emitting end face 11a of the semiconductor laser medium 11 opposite to the light emitting end face 11b and an optical fiber FB0 for externally guiding the wave.

The diffractive optics 13 is a reflection type element and functions as a dispersion element which disperses emitted light from the laser medium 11 by the wavelength. The diffractive light generated by the diffractive optics 13 travels toward the directions different by the wavelengths.

The polygon mirror 75 is provided a plurality of reflecting surfaces 75a so that a reflecting surface 75a opposed to the lens 74b reflects light in sequence and is rotated at a constant angular velocity by a drive means (not shown).

Light emitted from the light emitting end face 11b of the semiconductor laser medium 11 is dispersed by the diffractive optics 13 by the wavelengths λ1 ... λn after converted to parallel light by the collimating lens 12 and travels in different directions by the wavelengths. The light dispersed by the wavelengths is relayed by the lenses 74a and 74b to impinge upon the reflecting surface 75a of the polygon mirror 75.

In response to rotation of the polygon mirror 75, the angle between the reflecting surface 75a and the incident light changes and accordingly the light perpendicularly incident thereto by the reflecting surface 75a is selectively reflected as the return light. The return light travels along the reverse optical path to return to the semiconductor laser medium 11 by way of the lenses 74a and 74b, the diffractive optics 13 and the collimating lens 12. An external resonator having its opposite ends at the light emitting end face 11a of the semiconductor laser medium 11 and the reflecting surface 75a of the polygon mirror 75 is thus formed and light L is emitted from the light emitting end face 11a of the semiconductor laser medium 11. The oscillating wavelength of this light L is the wavelength of the return light.

The wavelength of the return light changes in response to rotation of the polygon mirror 75, and the wavelength sweeping of one period, from λ1 to λn, is effected for each of the reflecting surfaces 75a. Since a plurality of the reflecting surfaces 75a are provided at predetermined intervals, the wavelength sweeping is repeated at constant periods.

The lenses 74a and 74b are designed in their distortion so that the inverse of a number of the wavelength of the return light linearly changes with time in the laser 70. Since the wavelength λ, the frequency ν and the velocity of light c are in the relation of ν=c/λ, the wavelength sweeping in the optical tomography system 1 is arranged so that the frequency of the return light linearly changes with time, and the optical tomography system 2 after all sweeps the wavelength of the return light so that the frequency ν(t) of the return light linearly changes with time t during the sweeping time T corresponding to one period as shown in FIG. 9. In FIG. 9, the frequency of the return light at the sweeping initiating time (t=0) of each period is $\nu_0$, and the frequency of the return light at the sweeping ending time (t=T) of the period is $\nu_T$.

A method of designing the distortion in the lenses 74a and 74b will be described, hereinbelow.

When the distortion curve of the lens 74a is represented by formula
h=F(θ) wherein θ represents an angle of view and the distortion curve of the lens 74b is represented by formula
h=G(θ') wherein θ' represents an angle of view, $$\theta = F^{-1}\{G(\theta')\} \tag{1}$$

Since the polygon mirror is rotated at a constant angular velocity, $$\theta'(t) = \theta'_0 - \alpha t \tag{2}$$

wherein t=0 to T (T represents one period of wavelength sweeping) and α represents the angular velocity of the polygon mirror. Further, since the frequency ν(t) of the return light is proportional to the time t in the optical tomography system 2 of this embodiment, the following formulae are satisfied.

$$\nu(t) = \nu_0 + (\nu_T - \nu_0)/T \cdot t$$

$\theta(t) = 2\pi C/\nu(t)$ wherein ν changes from $\nu_0$ to $\nu_T$, when λ changes from λ0 to λT.

Since the light L has been diffracted by the diffractive optics 13, θ(t) and λ(t) can be represented by the following formula.

$$\sin\theta(t) = \sin\theta_0 + (\sin\theta_T - \sin\theta_0) \cdot (\lambda(t) - \lambda_0)/(\lambda_T - \lambda_0) \tag{3}$$

wherein when θ is $\theta_0$, λ is $\lambda_0$ and when θ is $\theta_T$, λ is $\lambda_T$.

Then F and G in the following formula are calculated to fit to the formula (3).

$$\theta(t) = F^{-1}\{G(\theta(t))\} \tag{4}$$

Formula (3) is substituted for θ(t) in the formula (4) and Formula (1) is substituted for θ'(t).

In order to realize this formula, the distortion curve of the lens 74a was taken as F(θ)=f·sin θ and the distortion curve of the lens 74b was taken as G(θ)=f·tan θ. $\theta_0$=0°, $\theta_T$=30°, $\lambda_0$=950 nm and $\lambda_T$=1150 nm.

It has been generally known that aberrations other than the distortion can be removed in these lenses. In the normal optical systems, there is never used a combination of lenses respectively having distortion curves F(θ)=f·sin θ and G(θ)=f·tan θ.

Figure 11:
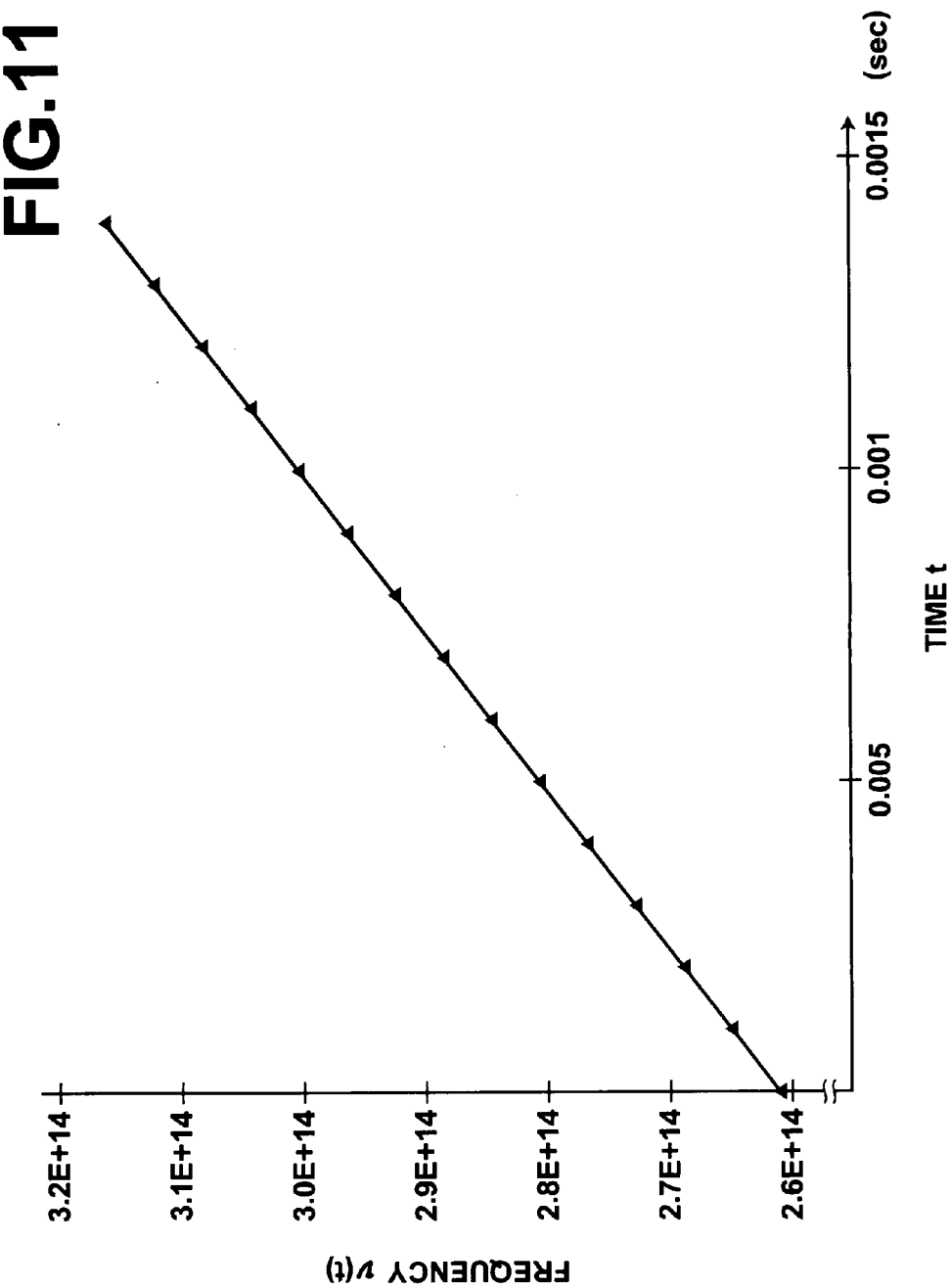
FIG. 11 is a view showing the relation between time and the oscillating frequency in the laser shown in FIG. 8.
Figure 12:
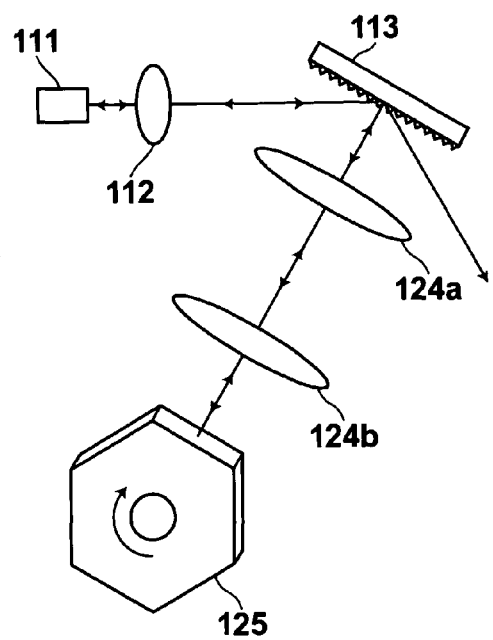
FIG. 12 is a view showing in brief a conventional wavelength tunable laser.
Figure 13:
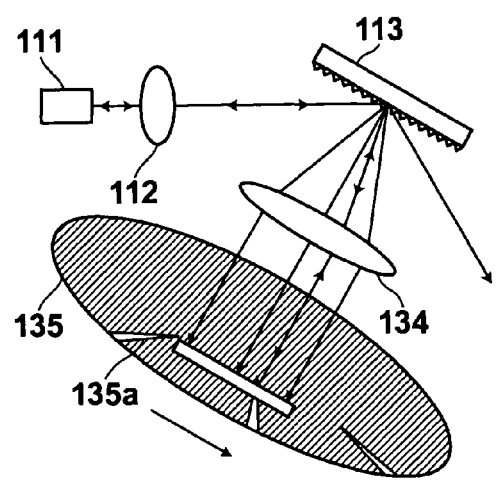
FIG. 13 is a view showing in brief a conventional wavelength tunable laser.
Figure 14:
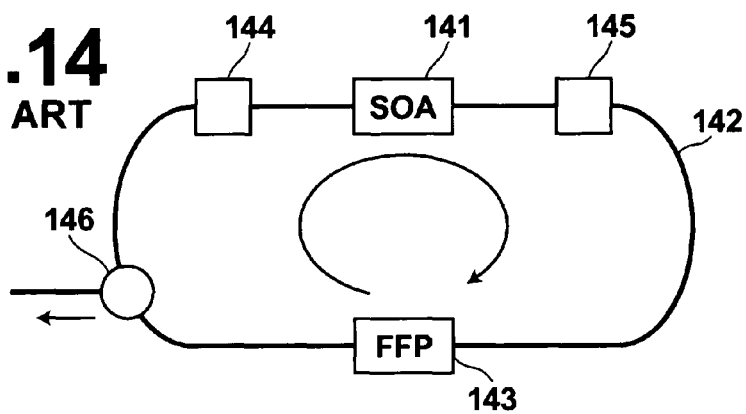
FIG. 14 is a view showing in brief a conventional wavelength tunable laser.
Figure 15:
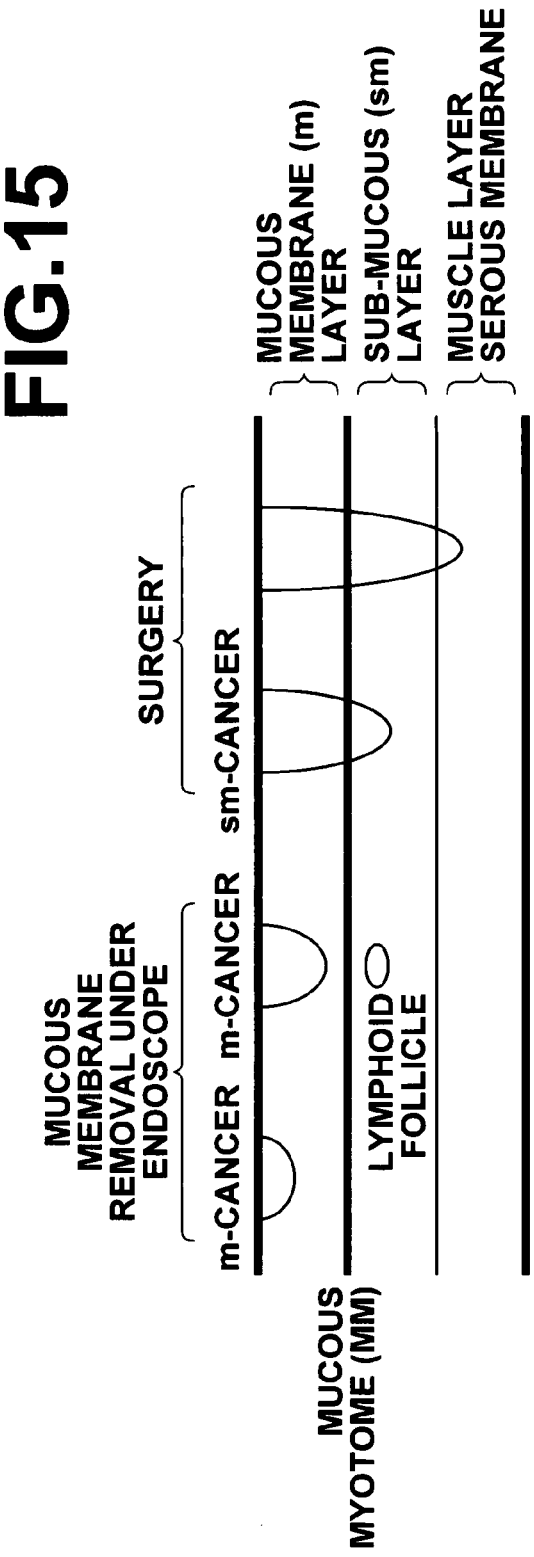
FIG. 15 is a view showing filtration of cancer in the stomach wall.
Figure 16:
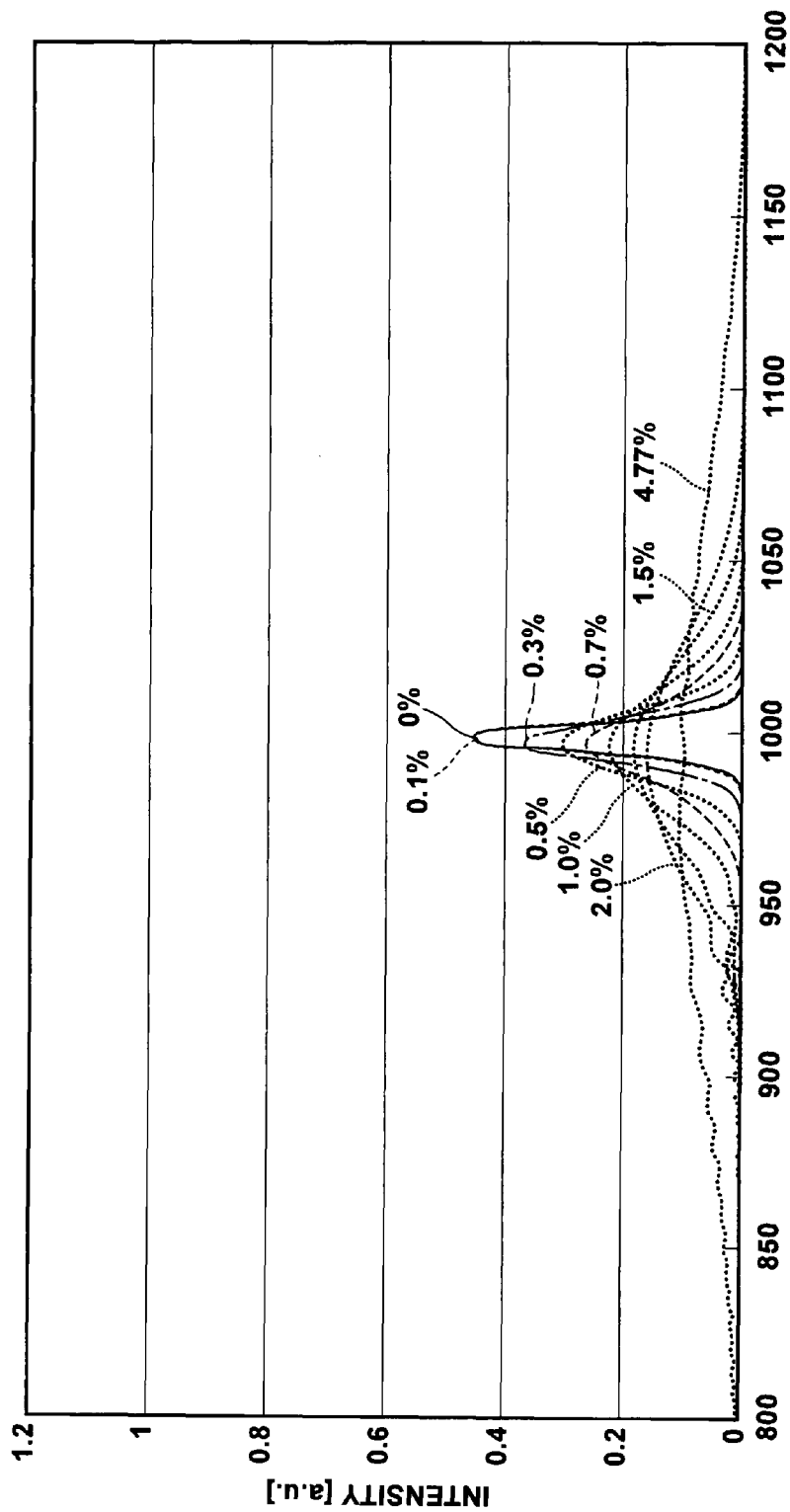
FIG. 16 is a view illustrating the relation between the linearity of the frequency change with time and the deterioration of signal when an optical tomographic image is to be obtained at the depth of 1 mm.

The sweeping time t, the oscillating frequency ν, $F^{-1}\{G(\theta(t))\}$ and the difference between the $F^{-1}\{G(\theta(t))\}$ and an ideal linear line in the above embodiment are shown in FIG. 10. As shown in FIG. 10, the maximum value of the difference is 0.191349, and the linearity of the frequency change= (0.191349/30)×100=0.64%, which is not larger than 0.7%. FIG. 11 shows a graph showing the relation between time and the oscillating frequency in the result of designing shown in FIG. 10.

As shown in FIGS. 10 and 11, the linearity of the frequency change is not larger than 0.7% in the laser 70 since distortion curve of the lens 74a is F(θ)=f·sin θ and distortion curve of the lens 74b is G(θ)=f·tan θ. By correcting the distortion curves of the lenses 74a and 74b to satisfy the above formula, it is possible to sweep the oscillating frequency so that the linearity of the frequency change is not larger than 0.4% or 0.1%.

Since being the same as those of the optical tomography system 1 shown in FIG. 1, the structure of the optical tomography system and an optical tomographic image obtaining action of the same are not described here.

As described above, in the optical tomography system 2 of the second embodiment, since the frequency of the oscillating light is linearly changed with time, data can be easily obtained so that the data distribution cannot be discrete and the data distribution with respect to the frequency is uniformly spaced when the frequency analysis is to be carried out, whereby the accuracy in the frequency-analysis can be improved as compared with the conventional. Further, when the linearity of the frequency change is not larger than 0.7%, the axial resolution can be not larger than 30 μm at a depth of 1 mm so long as measuring light with which the axial resolution of 10 μm can be obtained at a depth of 0 mm. Accordingly, the system is suitable for diagnosis of depth of cancer such as extraction of mucous myotome (MM) cancer, for instance, under an endoscope.

When, for instance, a pair of lenses which have been corrected to approach an ideal distortion curve where the inverse of a number of a wavelength of the return light perfectly linearly changes with time are employed in place of the lenses 74a and 74b in the wavelength tunable laser 70, the oscillating frequency is swept so that the linearity of the frequency change is not larger 0.4% or 0.1%, the deterioration of a signal at a depth of 1 mm is less and a high resolution optical tomographic image can be obtained to a deeper depth.

What is claimed is:

1. An external resonator type wavelength tunable laser comprising
    a laser medium,
    a dispersion means which spatially disperses light emitted from the laser medium by wavelength, and
    a wavelength selecting means having a reflecting surface which moves across the light which undergoes the wavelength dispersion by the dispersion means, and selectively reflects a part of the light which is reflected by the reflecting surface as a return light,
    the wavelength selecting means being structured so that the inverse of a number of a wavelength of the return light linearly changes with time, wherein
    the reflecting surface is partially formed in a body of rotation rotatable about a predetermined axis to extend substantially in a diametrical direction of the body of rotation like a curve to be concave toward the forward of the direction of rotation of the body of rotation.

2. An external resonator type wavelength tunable laser as defined in claim 1 in which lights dispersed by the wavelength by the dispersion means in a plane which includes the reflecting surface and is perpendicular to the predetermined axis are disposed on a linear line in a direction intersecting a diametrical direction of a body of rotation and the distances from the light of the wavelengths to the predetermined axis are simply decreased or increased.

3. An external resonator type wavelength tunable laser comprising
    a laser medium,
    a dispersion means which spatially disperses light emitted from the laser medium by wavelength,
    a rotating polygon mirror which selectively reflects a part of the light which is dispersed by wavelength by the dispersion means as a return light,
    a distortion generating means disposed between the dispersion means and the rotating polygon mirror,
    the distortion generating means generating a distortion so that the inverse of a number of a wavelength of the return light substantially linearly changes with time;
    a lens group comprising at least two lenses is disposed between the dispersion means and the rotating polygon mirror and the lens group doubles as the distortion generating means; and
    the lens group comprises a pair of lenses, one being $F(\theta)=f\cdot\sin\theta$ in a distortion curve, the other being $G(\theta)=f\cdot\tan\theta$ in a distortion curve.

4. An external resonator type wavelength tunable laser as defined in claim 3 in which the distortion generating means generates a distortion where the inverse of a number of a wavelength of the return light gives a linearity of not larger than 0.7% to time within a predetermined rotating angle of the rotating polygon mirror.

5. An external resonator type wavelength tunable laser as defined in claim 3 in which the distortion generating means generates a distortion where the inverse of a number of a wavelength of the return light gives a linearity of not larger than 0.7% to time within a predetermined rotating angle of the rotating polygon mirror.

6. An external resonator type wavelength tunable laser as defined in claim 3 in which the distortion generating means generates a distortion where the inverse of a number of a wavelength of the return light gives a linearity of not larger than 0.7% to time within a predetermined rotating angle of the rotating polygon mirror.

* * * * *